United States Patent
Stern et al.

(10) Patent No.: US 7,135,455 B2
(45) Date of Patent: Nov. 14, 2006

(54) METHODS FOR THE THERAPEUTIC USE OF CYCLOSPORINE COMPONENTS

(75) Inventors: Michael E. Stern, Mission Viejo, CA (US); David Power, Trabuco Canyon, CA (US)

(73) Assignee: Allergan, Inc, Irvine, CA (US)

( * ) Notice: Subject to any disclaimer, the term of this patent is extended or adjusted under 35 U.S.C. 154(b) by 0 days.

(21) Appl. No.: 10/990,054

(22) Filed: Nov. 15, 2004

(65) Prior Publication Data

US 2006/0105944 A1    May 18, 2006

(51) Int. Cl.
A61K 38/12    (2006.01)
(52) U.S. Cl. ...................................................... 514/11
(58) Field of Classification Search .................. None
See application file for complete search history.

(56) References Cited

U.S. PATENT DOCUMENTS

| | | | |
|---|---|---|---|
| 3,278,447 A | 10/1966 | McNicholas | |
| 4,388,307 A | 6/1983 | Cavanak | |
| 4,614,736 A * | 9/1986 | Delevallee et al. | 514/179 |
| 4,649,047 A | 3/1987 | Kaswan | |
| 4,814,323 A | 3/1989 | Andrieu | |
| 4,839,342 A | 6/1989 | Kaswan | |
| 4,970,076 A | 11/1990 | Horrobin | |
| 4,990,337 A | 2/1991 | Kurihara et al. | |
| 4,996,193 A | 2/1991 | Hewitt et al. | |
| 5,286,730 A | 2/1994 | Caufield et al. | |
| 5,286,731 A | 2/1994 | Caufield et al. | |
| 5,342,625 A | 8/1994 | Hauer et al. | |
| 5,368,854 A * | 11/1994 | Rennick | 424/85.2 |
| 5,411,952 A | 5/1995 | Kaswan | |
| 5,474,979 A | 12/1995 | Ding et al. | |
| 5,504,068 A | 4/1996 | Komiya et al. | |
| 5,540,931 A | 7/1996 | Hewitt et al. | |
| 5,719,123 A | 2/1998 | Morley et al. | |
| 5,739,105 A | 4/1998 | Kim et al. | |
| 5,807,820 A | 9/1998 | Elias | |
| 5,843,452 A | 12/1998 | Wiedmann et al. | |
| 5,843,891 A | 12/1998 | Sherman | |
| 5,858,401 A | 1/1999 | Bhalani et al. | |
| 5,866,159 A | 2/1999 | Hauer et al. | |
| 5,891,846 A | 4/1999 | Ishida et al. | |
| 5,916,589 A | 6/1999 | Hauer et al. | |
| 5,951,971 A | 9/1999 | Kawashima et al. | |
| 5,962,017 A | 10/1999 | Hauer et al. | |
| 5,981,479 A | 11/1999 | Ko et al. | |
| 5,981,607 A | 11/1999 | Ding et al. | |
| 5,998,365 A | 12/1999 | Sherman | |
| 6,008,191 A | 12/1999 | Singh et al. | |
| 6,008,192 A | 12/1999 | Al-Razzak et al. | |
| 6,022,852 A | 2/2000 | Klokkers et al. | |
| 6,024,978 A | 2/2000 | Hauer et al. | |
| 6,046,163 A | 4/2000 | Stuchlik et al. | |
| 6,159,933 A | 12/2000 | Sherman | |
| 6,254,860 B1 | 7/2001 | Garst | |
| 6,323,204 B1 | 11/2001 | Burke et al. | |
| 6,346,511 B1 | 2/2002 | Singh et al. | |
| 6,350,442 B1 | 2/2002 | Garst | |
| 6,413,547 B1 | 7/2002 | Bennett et al. | |
| 6,420,355 B1 | 7/2002 | Richter et al. | |
| 6,468,968 B1 | 10/2002 | Cavanak et al. | |
| 6,486,124 B1 | 11/2002 | Olbrich et al. | |
| 2001/0014665 A1 | 8/2001 | Fisher et al. | |
| 2003/0021816 A1 | 1/2003 | Kang et al. | |
| 2003/0044452 A1 | 3/2003 | Ueno | |
| 2003/0055028 A1 * | 3/2003 | Stergiopoulos et al. | 514/179 |
| 2003/0060402 A1 | 3/2003 | Cavanak et al. | |
| 2003/0087813 A1 | 5/2003 | Or et al. | |
| 2003/0104992 A1 | 6/2003 | Or et al. | |
| 2003/0109425 A1 | 6/2003 | Or et al. | |
| 2003/0109426 A1 | 6/2003 | Or et al. | |
| 2003/0143250 A1 | 7/2003 | Hauer et al. | |

FOREIGN PATENT DOCUMENTS

WO    WO 03/030834    4/2003

OTHER PUBLICATIONS

T.A. Winter, et al. Scand J Gastroenterol. (1993), 28(8), pp. 701-704.*
M. Schwab and U. Klotz, Clin. Pharmacokinet. (2001), 40(10), pp. 723-751.*
J. Rudinger. In: Peptide Hormones, JA Parsons, Ed. (1976), pp. 1-7.*
D.E. Smilek, et al. Proc. Natl. Acad. Sci. USA (1991) 88, pp. 9633-9637.*
M Banić, et al. Dig. Dis. Sci. (2002), 47(6), pp. 1362-1368.*
The Online Medical Dictionary, accessed Jul. 7, 2005. 5 pages.*
W.J. Sandborn, et al. Am. J. Gastroenterol. (1993), 88(5), pp. 640-645.*
D.H. Present. Am. J. Gastroenterol. (1993), 88(5), pp. 627-630.*
S. Ardizzone and G.B. Porro. Drugs. (1998), 55(4), pp. 519-542.*
W.J. Sandborn, et al. Gastroenterology. (1994), 106(6), pp. 1429-1435.*
Acheampong et al, "Cyclosporine Distribution into the Conjunctiva, Cornea, Lacrimal Gland, and Systemic Blood Following Topical Dosing of Cyclosporine to Rabbit, Dog, and Human Eyes," *Lacrimal Gland, Tear Film, and Dry Eye Syndromes 2—Basic Science and Clinical Relevance*, Plenum Press, New York & London, © 1998, pp. 1001-1004.
Acheampong et al, "Distribution of Cyclosporin A in Ocular Tissues After Topical Administration to Albino Rabbits and Beagle Dogs," *Curr Eye Res*, Feb. 1999, 18(2):91-103b.

(Continued)

*Primary Examiner*—Bruce R. Campell
*Assistant Examiner*—Andrew D. Kosar
(74) *Attorney, Agent, or Firm*—Stout, Uxa, Buyan & Mullins, LLP; Frank J. Uxa

(57) ABSTRACT

Methods of treating humans or animals having various conditions are disclosed which include administering a cyclosporine component. Among the conditions treated are dry mouth syndrome, verruciform xanthoma, achlorhydria, mucous cysts, oral submucous fibrosis, oral nevi, cancer of the oral mucosa, maloplakia of the genito-urinary tract, vulvovaginitis, helicobacter plylori infection, duodenal ulcers, peptic ulcers, conditions affecting the uterus and appendicitis.

13 Claims, No Drawings

OTHER PUBLICATIONS

Angelov et al, "Preclinical Safety Studies of Cyclosporine Ophthalmic Emulsion," *Lacrimal Gland, Tear Film, and Dry Eye Syndromes 2—Basic Science and Clinical Relevance*, Plenum Press, New York & London, © 1998, pp. 991-995.

Brewster et al, "Enhanced Delivery of Ganciclovir to the Brain through the Use of Redox Targeting," *Antimicrobial Agents and Chemotherapy*, Apr. 1994, 38(4):817-823.

Brewster et al, "Intravenous and Oral Pharmacokinetic Evaluation of a 2-Hydroxypropyl-β-cyclodextrin-Based Formulation of Carbamazepine in the Dog: Comparison with Commercially Available Tablets and Suspensions," *J Pharm Sci*, Mar. 1997, 86(3):335-9.

Brewster et al, "Preparation, Characterization, and Anesthetic Properties of 2-Hydroxypropyl-β-cyclodextrin Complexes of Pregnanolone and Pregnenolone in Rat and Mouse," *J Pharm Sci*, Oct. 1995, 84(10):1154-9.

Sall et al, "Two Multicenter, Randomized Studies of the Efficacy and Safety of Cyclosporine Ophthalmic Emulsion in Moderate to Severe Dry Eye Disease. CsA Phase 3 Study Group," *Ophthalmology*, Apr. 2000, 107(4):631-9.

Small et al,"Blood Concentrations of Cyclosporin A During Long-Term Treatment With Cyclosporin A Ophthalmic Emulsions in Patients With Moderate to Severe Dry Eye Disease," *J Ocul Pharmacol Ther*, Oct. 2002, 18(5):411-8.

Stevenson et al., "Efficacy and Safety of Cyclosporin A Ophthalmic Emulsion in the Treatment of Moderate-to-severe Dry Eye Disease," *Ophthalmology*, May 2000, 107(5):967-74.

Gaeta G M et al: "Cyclosporin bioadhesive gel in the topical treatment of erosive lichen planus" International Journal of Immunopathology and Pharmacology, vol. 7, No. 2, 1994, pp. 125-132.

Gunduz et al, "Topical Cyclosporin Treatment of Keratoconjunctivitis Sicca in Secondary Sjogren's Syndrome", Acta Ophthalmologica, vol. 72, No. 4, 1994, pp. 438-442, XP009063039.

Phillips et al, "Cyclosporine Has A Direct Effect on the Differentiation of a Mucin-Secreting Cell Line", Journal of Cellular Physiology, vol. 184, No. 3, Sep. 2000, pp. 400-408, XP009063023.

Gipson et al, "Character of Ocular Surface Mucins and Their Alteration in Dry Eye Disease", The Ocular Surface, vol. 2, No. 2, Apr. 2004, pp. 131-148, XP001208377.

Akped et al, "A Randomized Trial of Topical Cyclosporin 0.05% in Topical Steriod-Resistant Atopic Keratoconjunctivitis", Ophthalmology, vol. III, No. 3, Mar. 2004, pp. 476-482, XP009063021.

Eisen et al, "Topical Cyclosporine for Oral Mucosal Disorders", Journal of the American Academy of Dermatology, vol. 23, No. 6, Part 2, Dec. 1990, pp. 1259-1264, XP009063043.

Epstein et al, "Topical Cyclosporine in a Bioadhesive for Treatment of Oral Lichenoid Mucosal Reactions. An Open Label Clinical Trail", Oral Surgery, Oral Medicine . . . , vol. 82, No. 5, 1996, pp. 532-536, XP009063045.

Erdmann et al, "Pemphigus Vulgaris Der Mund-Und Kehlopfschleimhaut Pemphigus Vulgaris of the Oral Mucosa and the Larynx", H+G Zeitschrift Fuer Hautkrankheiten, vol. 72, No. 4, 1997, pp. 283-296, XP009063042.

Brinkmeier et al, "Pyodermatitis-Pyostomatitis Vegetans: A Clinical Course of Two Decades with Response to Cyclosporine and Low-Dose Prednisolone", Acta Dermato-Venereologica, vol. 81, No. 2, May 2001, pp. 134-136.

Gremse et al, "Ulcerative Colitis in Children. Medical Management", Pediatric Drugs, vol. 4, No. 12, 2002, pp. 807-815, XP009063025.

* cited by examiner

METHODS FOR THE THERAPEUTIC USE OF CYCLOSPORINE COMPONENTS

The present invention relates to methods of providing desired therapeutic effects to humans or animals using compositions including cyclosporine components. More particularly, the invention relates to methods including administering to a human or animal afflicted with at least one of certain conditions a therapeutically effective amount of a cyclosporine component to provide a desired therapeutic effect.

The use of cyclosporin-A and cyclosporin A derivatives to treat ophthalmic conditions has been the subject of various patents, for example Ding et al U.S. Pat. No. 5,474,979; Garst U.S. Pat. No. 6,254,860; and Garst U.S. Pat. No. 6,350,442, this disclosure of each of which is incorporated in its entirely herein by reference. In addition, a number of prior art patents have disclosed the use of cyclosporine, administered topically and/or systemically, as a treatment for other conditions and/or diseases.

However, there are additional conditions which afflict humans and/or animals.

It would be advantageous to provide methods of treating such additional conditions.

SUMMARY OF THE INVENTION

New methods of treating certain conditions in a human or animal have been discovered. The present methods provide substantial overall efficacy in providing the desired therapeutic effect or effects. In addition, other important benefits are obtained employing the present methods. For example, the present methods can be easily and effectively practiced by the prescribing physician and patient without causing substantial or undue patient stress. In short, the present methods provide substantial and acceptable overall efficacy, together with other advantages, such as ease of practice and reduced patient stress.

In one aspect of the present invention, the present methods comprise topically administering a therapeutically effective amount of a cyclosporine component to a human or animal having a condition selected from the group consisting of ulcerative colitis, inflammatory bowel disease, systemic lupus eryhematosis, rheumatoid arthritis, and multiple sclerosis.

In another aspect of the invention, the present methods comprise administering a therapeutically effective amount of a cyclosporine component to a human or animal having a condition selected from maloplakia of the skin, oral frictional hyperkeratosis, oral manifestations of autoimmune blistering disease, oral lichen planus, aphthous ulcers, nasal polyps, rhinosporiodosis, sinusitis, iritis, carcinoid lung, laryngitis and atrophic gastritis. The administering step is effective in treating the condition.

Each and every feature described herein, and each and every combination of two or more of such features, is included within the scope of the present invention provided that the features included in such a combination are not mutually inconsistent.

These and other aspects and advantages of the present invention are apparent in the following detailed description, examples and claims.

DETAILED DESCRIPTION

The present methods employ cyclosporine components to treat humans or animals, for example, other mammals, afflicted with various conditions. Among the conditions treated in accordance with the present invention are ulcerative colitis, inflammatory bowel disease, systemic lupus eryhematosis, rheumatoid arthritis, multiple sclerosis, maloplakia of the skin, oral frictional hyperkeratosis, oral manifestations of autoimmune blistering disease, oral lichen planus, aphthous ulcers, nasal polyps, rhinosporiodosis, sinusitis, iritis, carcinoid lung, laryngitis and atrophic gastritis.

In general, the present methods comprise administering a therapeutically effective amount of a cyclosporine component to a human or animal having a condition to be treated. The term "condition" as used herein includes, without limitation, one or more injuries, diseases, illnesses, other conditions and the like. The administering step is effective to treat the condition. A condition is treated in accordance with the present invention when, for example and without limitation, as a result of the present administering step, one or more symptoms of the condition is reduced in severity or eliminated, the progression of the condition is slowed or stopped or reversed, the condition itself is reduced in severity or substantially (or totally) resolved and the like therapeutic benefits.

In one embodiment, the present administering step comprises topically administering the cyclosporine component to the affected area, for example, the affected mucosal tissue, of the human or animal. Topical administration allows a therapeutically effective amount of the cyclosporine component to be administered to treat a condition, without subjecting the remainder of the human or animal to the cyclosporine component. Topical administration of a cyclosporine component in accordance with the present invention is particularly advantageous in treating conditions selected from ulcerative colitis, inflammatory bowel disease, systemic lupus eryhematosis, rheumatoid arthritis, and multiple sclerosis.

Employing reduced systemic or blood concentrations of cyclosporine component, as in one embodiment of the present invention, is advantageously effective to treat the condition/disease under treatment, preferably with substantially no detectable concentration of the cyclosporine component in the blood of the human or animal being treated. The cyclosporine component concentration of blood can be advantageously measured using a validated liquid chromatography/mass spectrometry-mass spectrometry (VLC/MS—MS) analytical method, such as described elsewhere herein.

In one embodiment, in the present methods the blood of the human or animal has concentrations of cyclosporine component of 0.1 ng/ml or less.

In one embodiment, the cyclosporine component may be administered to a human or animal as part of the combination treatment to treat a condition of the human or animal. For example, the cyclosporine component may be administered to the human or animal along with one or more other therapeutic agents effective in treating the condition of the human or animal. The other therapeutic agent or agents can be administered to the human or animal in the same composition with the cyclosporine component or in a different composition from the cyclosporine component. Examples of useful other therapeutic components include, without limitation, antibiotics, various pain medications, anti-inflammatory medications and the like and mixtures thereof.

Alternatively, or in addition, the cyclosporine component may be administered to a human or animal in conjunction with, for example, prior to, during and/or after, one or more surgical procedures to treat the condition. Such administration of the cyclosporine component may facilitate the surgical procedure(s), for example, and without limitation, by controlling and/or otherwise treating the condition prior to the procedure(s), by making the procedure(s) easier to tolerate and/or less stressful during the procedure(s), and by reducing recovery time and/or enhancing extent of recovery from the surgical procedure(s) after the procedure(s).

Any suitable cyclosporine component effective in the present methods may be used.

Cyclosporines are a group of nonpolar cyclic oligopeptides with known immunosuppressant activity. Cyclosporin A, along with several other minor metabolites, as well as cyclosporin B, C, D, E, F, G, H, I, J, K, L, M, N, O, P, Q, R, S, T, U, V, W, X, Y and Z, have been identified. In addition, derivatives, salts and the like of such cyclosporines and a number of synthetic analogs have been prepared and may be useful in the present invention. See, for example, the Garst Patents noted elsewhere herein.

In general, commercially available cyclosporines may contain a mixture of several individual cyclosporines which all share a cyclic peptide structure consisting of eleven amino acid residues with a total molecular weight of about 1,200, but with different substituents or configurations of some of the amino acids.

The term "cyclosporine component" as used herein is intended to include any individual member of the cyclosporine group, salts thereof, derivatives thereof, analogs thereof and mixtures thereof, as well as mixtures of two or more individual cyclosporines salts thereof, derivatives thereof, analogs thereof and mixtures thereof.

Particularly preferred cyclosporine components include, without limitation, cyclosporin A, derivatives of cyclosporin A, salts of cyclosporin A and the like and mixtures thereof. Cyclosporin A is an especially useful cyclosporine component.

The chemical structure for cyclosporin A is represented by Formula 1

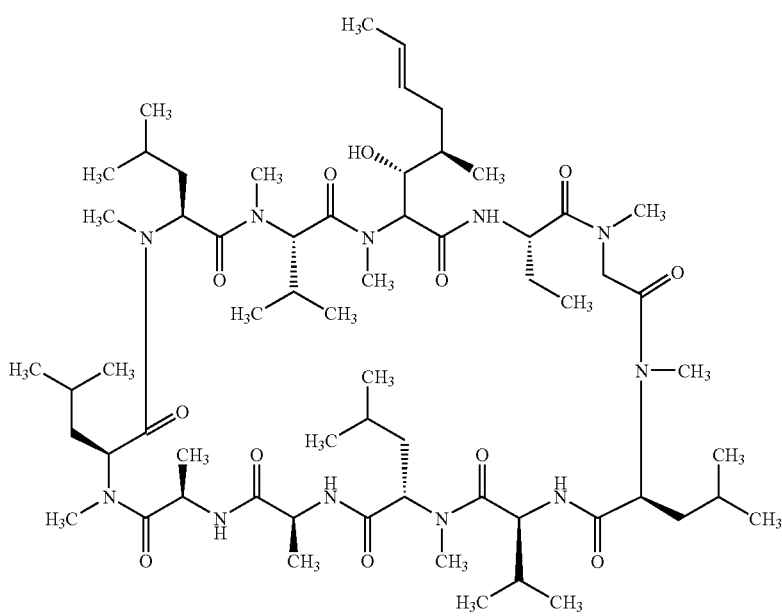

Formula I

As used herein the term "derivatives" of a cyclosporine refer to compounds having structures sufficiently similar to the cyclosporine so as to function in a manner substantially similar to or substantially identical to the cyclosporine, for example, cyclosporin A, in the present methods. Included, without limitation, within the useful cyclosporin A derivatives are those selected from ((R)-methylthio-Sar)$^3$-(4'-hydroxy-MeLeu) cyclosporin A, ((R)-(Cyclo)alkylthio-Sar)$^3$-(4'-hydroxy-MeLeu)$^4$-cyclosporin A, and ((R)-(Cyclo)alkylthio-Sar)$^3$-cyclosporin A derivatives described below.

These cyclosporine derivatives are represented by the following general formulas (II), (III), and (IV) respectively:

Formula II
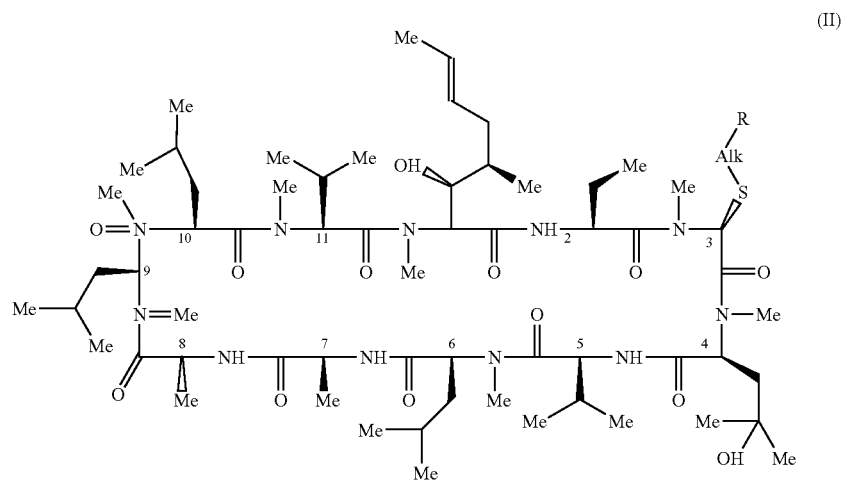
Formula III
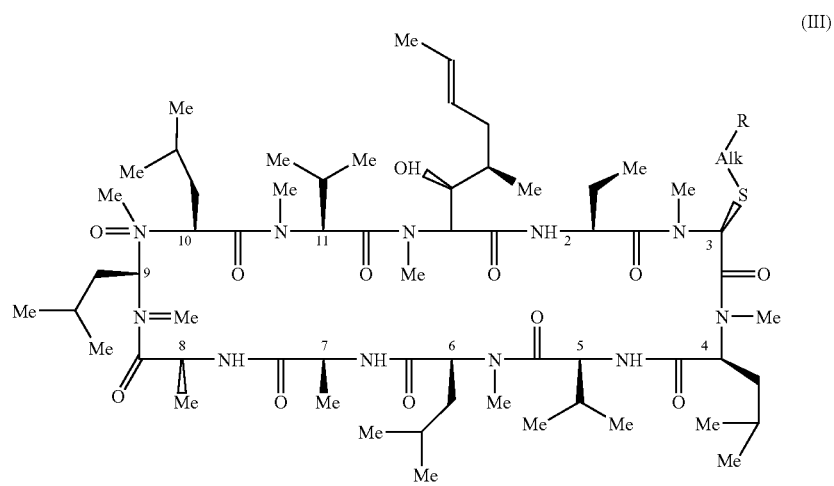
Formula IV
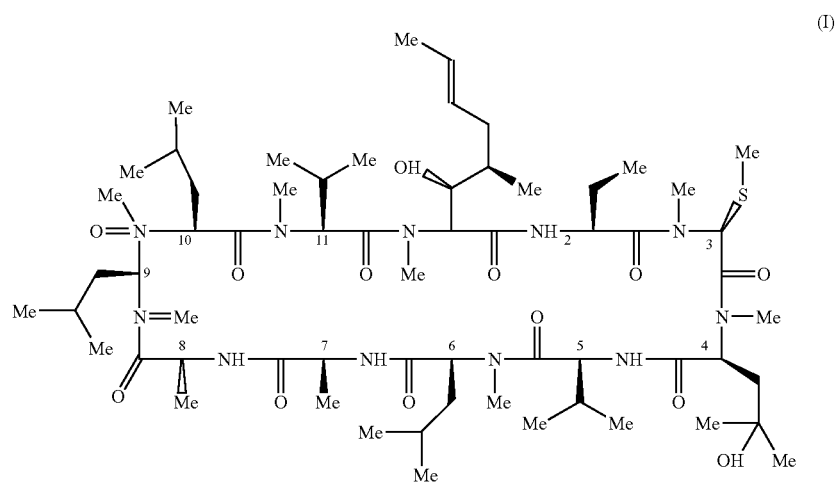

wherein Me is methyl; Alk is 2–6 C alkylene or 3–6 C cycloalkylene; R is OH, COOH, alkoxycarbonyl, —NR$_1$R$_2$ or N(R$_3$)—(CH$_2$)—NR$_1$R$_2$; wherein R$_1$,R$_2$ is H, alkyl, 3–6 C cycloalkyl, phenyl (optionally substituted by halo, alkoxy, alkoxycarbonyl, amino, alkylamino or dialkylamino), benzyl or saturated or unsaturated heterocyclyl having 5 or 6 members and 1–3 heteroatoms; or NR$_1$R$_2$ is a 5 or 6 membered heterocycle which may contain a further N, O or S heteroatom and may be alkylated; R$_3$ is H or alkyl and n is 2–4; and the alkyl moieties contain 1–4 C.

The present methods may be practiced employing any suitable compositions or combinations of compositions including therapeutically effective amounts of cyclosporine component. The cyclosporine component is present in an amount effective to provide the desired therapeutic effect when the cyclosporine-containing composition is administered to a human or animal in accordance with the present invention. The cyclosporine component advantageously is present in the compositions in amounts ranging from about 0.03% to about 15% or about 20% or more by weight of the composition. In one embodiment, the cyclosporine component is present in an amount of about 0.1% to about 5% or about 10% or about 15% by weight of the composition. It is intended, however, that the choice of a particular amount of cyclosporine component is to be made in accordance with factors well known in the medicinal arts, including mode of administration, the size and condition of the human or animal and the type and severity of the condition to be treated.

The presently useful compositions may be liquids, suspensions, emulsions, semi-solids, capsules, gels, lotions, creams and the like. Those skilled in the art of pharmaceutical formulation are able to formulate suitable compositions including cyclosporine components in a suitable form, such as those forms noted herein, for example, including one or more pharmaceutically acceptable excipients, such as those conventionally used in similar compositions. Of course, care should be taken to use composition components which are compatible with the cyclosporine component being used and which do not unduly or significantly interfere with the administering step in which the composition is being used or with the human or animal being treated.

For example, cyclosporine components can be combined with carriers which form emulsions upon mixing with water. Such emulsions are described, for example, and without limitation, in Cavanak U.S. Pat. No. 4,388,307, the disclosure of which is hereby incorporated in its entirety herein by reference. Carriers, for example, and without limitation, glyceride carriers, may assist in alleviating problems of physical instability such as precipitation of the cyclosporine component from solution, and may also enable higher blood plasma concentrations, if desired.

In a useful embodiment, the presently useful compositions include hydrophobic components. Any suitable hydrophobic component may be employed in the present invention. Advantageously, the cyclosporine component is solubilized in the hydrophobic component. In one embodiment, the hydrophobic component may be considered as comprising a discontinuous phase in the presently useful cyclosporine component-containing compositions, for example, oil-in-water emulsions.

The hydrophobic component may be present in an effective amount, for example, in an amount of up to about 1.0% by weight or about 1.5% by weight or more of the composition.

Preferably, the hydrophobic component comprises one or more oily materials. Examples of useful oil materials include, without limitation, vegetable oils, animal oils, mineral oils, synthetic oils and the like and mixtures thereof. In a very useful embodiment, the hydrophobic component comprises one or more higher fatty acid glycerides. Excellent results are obtained when the hydrophobic component comprises castor oil.

Other useful cyclosporine component-containing compositions comprise the cyclosporine component in admixture with an emulsifying amount of a fatty acid glyceride, such as castor oil and the like, and a surfactant, such as polysorbate 80. Such compositions are described in Ding et al U.S. Pat. No. 5,474,979, the disclosure which is hereby incorporated in its entirety herein by reference. Also see Kaswan U.S. Pat. No. 4,649,047 and Kaswan U.S. Pat. No. 5,411,952, the disclosure of each of which is hereby incorporated in its entirety herein by reference.

In one embodiment, the presently useful compositions are self-emulsifying which, when exposed to an aqueous medium, form fine oil-in-water emulsions with little or no agitation. The property of self-emulsification permits such formulations to be administered in concentrated form, as for example in a hard gelatin or soft elastic capsules, with the expectation that a fine emulsion will be formed in the digestive tract. Additionally, emulsions may be prepared by combining a self-emulsifying pre-concentrate with an aqueous medium.

Previously-disclosed self-emulsifying systems include those in which a cyclosporine component is combined with mixtures of (i) medium-chain triglycerides and nonionic surfactants, (ii) vegetable oils and partial glycerides, such as polyglycolized glycerides or medium-chain mono- and diglycerides, or (iii) vegetable oils and nonionic surfactants such as polysorbate 80 or PEG-25 glyceryl trioleate.

In certain self-emulsifying formulations, a "microemulsion preconcentrate" of a cyclosporine component is formed by combining the cyclosporine component with (I) a hydrophilic phase, (II) a lipophilic phase, and (III) a surfactant, as well as optional thickeners, antioxidants or other excipients. Examples of such compositions are disclosed in Hauer et al U.S. Pat. No. 5,342,625, the disclosure which is hereby incorporated in its entirety herein by reference.

In addition, suitable compositions may include cyclosporine components in combination with a hydrophilic solvent phase and one or more surfactants, but not containing lipophilic solvents. Such cyclosporine component-containing formulations may be stable, simple to prepare, and have good pharmacokinetic properties.

As used herein, the terms "binary system", "binary composition" and "binary system of excipients" denote those cyclosporine component-containing formulations and compositions which contain, in addition to the cyclosporine component, a combination of at least one hydrophilic solvent and at least one surfactant, but which lack a lipophilic solvent. Such compositions may be supplemented with additional adjuvants and still be considered "binary", so long as they do not include a lipophilic solvent phase.

To prepare such pharmaceutical compositions, a binary system is combined with a cyclosporine component. The hydrophilic phase may comprise one or more of the known pharmaceutically acceptable hydrophilic solvents or excipients that are capable of solubilizing the cyclosporine component. Suitable classes of hydrophilic compounds include, for example and without limitation, pharmaceutically acceptable alcohols including the polyethylene glycols.

Examples of hydrophilic phase components useful in the presently useful compositions include, but are not limited to, water, ethanol, benzyl alcohol, propylene glycol, low molecular weight polyethylene glycols having a molecular weight of up to about 1,000, glycol, dimethyl isosorbide and the like and mixtures thereof.

The compositions may be prepared as semi-solids and placed into hard gelatin rather than soft elastic capsules, to allow for the use of ethanol and similar solvents.

The hydrophilic phase, comprising one or more hydrophilic solvents, typically comprises about 10% to about 90% by weight of the pharmaceutical composition. The precise amount used will vary depending on the nature of the hydrophilic compound or compounds used, the amount of cyclosporine component present, the dosage form, the condition being treated and other factors known in the art. Preferably the hydrophilic phase comprises about 20% to about 80%, and more preferably about 30% to about 60%, by weight of the composition. Where non-aqueous hydrophilic components are used, water can be included in the formulation at levels varying from about 0.5% to about 10%, or preferably from about 1% to about 5%, based on total weight of the composition.

Any of the known pharmaceutically acceptable surfactants may be used, including nonionic, anionic, cationic, and combinations thereof. Nonionic surfactants are preferred, and especially those surfactants having a hydrophile/lipophile balance (HLB) of 10 or more. Alternatively, certain combinations of high- and low-HLB surfactants may be utilized; preferably, such mixed surfactants are used in ratio such that the aggregate surfactant HLB (when weighted according to proportions used) remains in excess of 10.

Examples of suitable surfactants include, but are not limited to, polyoxyethylene derivatives of natural or hydrogenated vegetable oils such as castor oil; polyoxyethylenesorbitan fatty acid esters, such as mono-, di- and tri-lauryl, palmityl, stearyl and oleyl esters; alkyl/dialkyl sulfate, sulfonate or sulfosuccinate salts such as sodium lauryl sulfate and dioctyl sodium sulfosuccinate; polyoxyethylene fatty acid esters; phospholipids such as lecithins; transesterification products of natural vegetable oil triglycerides and polyalkylene polyols; sorbitan fatty acid esters; pentaerythritol fatty acid esters; polyoxyethylene glycol alkyl ethers and esters; and the like. The surfactants may be used alone or in combination.

Examples of specific surfactants which may be used include, without limitation, polyoxyethylene castor oil derivatives, such as polyoxyethylene glycerol triricinoleate polyoxyl 35 castor oil (CREMOPHOR® EL, available from BASF Corporation), and polyoxyl 40 hydrogenated castor oil (CREMOPHOR® RH40, available from BASF Corporation); mono-fatty acid esters of poloxyethylene (20) sorbitan, such as polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), and polyoxyethylene (20) sorbitan monolaurate (TWEEN® 20) (all available from ICI Surfactants, Wilmington, Del.); polyoxyethylene glycol 200 monostearate (MYRJ® 52, available from Calgene Chemicals, Skokie, Ill.); polyglycerol esters with a HLB of 10 or greater, such as decablyceryl mono- and dioleate and the like; and mixtures thereof.

In some instances (as when the compositions are prepared as semi-solids), it may be advantageous to use at least one additional low-HLB surfactant along with one or more of the above high-HLB surfactant. Examples of low-HLB auxiliary surfactants which may be used include, but are not limited to, polyglycerol oleates (such as CAPROL® 10G40); lecithins; glyceryl monooleate or monolinoleate mixtures (such as MYVEROL® 18-99 or 18-92); propylene glycol laurate; and sorbitan oleates such as sorbitan monooleate (SPAN® 80), sorbitan trioleate (SPAN® 85), and sorbitan sesquioleate (SPAN® 20) (all available from ICI Surfactants, Wilmington, Del.).

The surfactant phase may comprise about 10% to 90% by weight of the composition. Preferably the surfactant comprises about 20% to about 70% of the composition, and more preferably about 40% to about 60%, by weight.

If desired, the presently useful compositions may additionally comprise other pharmaceutically acceptable excipients, such as tonicity components, buffer components, polyelectrolyte components, thickeners, fillers, diluents, flavoring agents, coloring agents, antioxidants, preservatives, such as antibacterial or antifungal agents, acids and/or basis to adjust pH, and the like and mixtures thereof. Such additives, if present, may typically comprise about 0.01% to about 10% by weight of the composition. Such additives include those additives which are conventional and/or well known for use in similar pharmaceutical compositions. For example, suitable thickening agents include any of those known in the art, as for example pharmaceutically acceptable polymers and/or inorganic thickeners. Such agents include, but are not limited to, polyacrylate homo- and co-polymers; celluloses and cellulose derivatives; polyvinyl pyrrolidones; polyvinyl resins; silicates; and the like and mixtures thereof.

When desired, the cyclosporine-containing compositions may be prepared as semi-solid rather than liquid formulations by addition a greater proportion of appropriate thickening or solidifying agents. As noted above, such preparations may be particularly useful as fills for hard gelatin (as opposed to soft gelatin) capsules. Solidifiers suitable for the preparation of semi-solid compositions include, but are not limited to, polyethylene glycols having a molecular weight of more than about 1,000, such as PEG 1450 and PEG 3350; stearyl alcohol; and colloidal silicon dioxide (CAB-O-SIL® M-5, available from Cabot, Tuscola, Ill.). A semi-solid state may be often obtained by adding between about 8% or about 10% and about 15% or about 25% by weight solidifying agent. The actual amount of solidifying agent needed will depend on the physical characteristics of the other excipients which are present.

Except as otherwise noted elsewhere herein, the cyclosporine component-containing compositions may be administered topically and/or systemically, for example, by any of the methods known in the art. Such methods include, but are not limited to, systemic administration, for example, oral administration of a suspension formed by mixing a cyclosporine component-containing composition with an aqueous medium such as water, milk or juice; a cyclosporine component-containing composition placed in a soft elastic or hard gelatin capsule; parenteral administration including intravenous, intramuscular, intraperitoneal, intrasternal, subcutaneous and intraarticular injection or infusion of a cyclosporine component-containing composition; and/or topical administration methods, such as topical administration of ointments, drops, solutions, suspensions or emulsions including a cyclosporine component. Topical formulations, intended for topical administration to the affected tissue area or areas, may be prepared directly, or by combining a cyclosporine component-containing concentrate with a diluent, for example, an aqueous diluent. Such topical formulations may include additional excipients as necessary, for example, to modify consistency of the rate of absorption of the cyclosporine component.

In preparing the presently useful compositions, the components may be combined in any order with mixing or light agitation to ensure complete blending.

The cyclosporine component may be administered in a sufficient amount, and for a sufficient time, as required to provide the desired therapeutic effect. The specific therapeutically effective dosage level may be dependent on a number of factors including the specific condition to be treated, the severity of the condition, the activity of the particular cyclosporine component being employed, the specific cyclosporine component-containing composition employed, the time and method of administration, the duration of treatment, and other factors which are well known in the medical arts.

The following non-limiting examples illustrate certain aspects of the present invention.

EXAMPLE 1

A male patient, age 51, suffering from ulcerative colitis is treated with a composition containing 0.3% by weight of cyclosporin A in a conventional carrier. The composition, in the form of a rectal suppository, is administered once daily for two weeks. After such administration, the patient reports that at least one symptom, for example, pain, associated with the ulcerative colitis is reduced in severity.

EXAMPLE 2

A male patient, age 44, suffering from inflammatory bowel disease is treated with a composition containing 0.3% by weight of cyclosporin A in a conventional carrier. The composition, in the form of a rectal suppository, is administered once daily for two weeks. After such administration, the patient reports that at least one symptom, for example, pain, associated with the inflammatory bowel disease is reduced in severity.

EXAMPLE 3

A female African American patient, age 45, is diagnosed with systemic lupus eryhematosis. The affected areas of the patient's body are treated topically with a cream containing 0.2% by weight of cyclosporin A in a conventional carrier twice daily for two weeks. Thereafter, the patient reports that the severity of the systemic lupus eryhematosis is reduced.

EXAMPLE 4

A female patient, age 52, suffering from rheumatoid arthritis is treated with a composition containing 0.2% by weight of cyclosporin A in a conventional carrier. The composition, in the form of a lotion, is administered topically to affected joint areas of the patient's body twice daily for one month. After such treatment, the patient reports reduced soreness and inflammation from the rheumatoid arthritis.

EXAMPLE 5

A female patient, age 36, diagnosed with multiple sclerosis experiences tightness and aching in her shoulders. She is treated with a cream composition containing 0.3% by weight of cyclosporin A in a conventional carrier. The composition is topically applied to her shoulders twice daily for one month. Such treatment reduces the tightness and aching caused by the multiple sclerosis.

EXAMPLE 6

A male patient, age 53, presents an ulceration on his thigh that is diagnosed as malakoplakia of the skin. The patient is treated with a combination of systemically administered antibiotic, such as quinolone and/or trimethoprin-sulfamethoxazole, and topically administered cyclosporin A. The cyclosporin A is administered to the affected area in the form of a lotion containing 0.3% by weight cyclosporin A in a conventional carrier. The cyclosporin A-containing lotion is administered twice daily for two weeks. The antibiotic is administered in 500 mg doses twice daily for two weeks. After this treatment, the ulceration is resolved.

EXAMPLE 7

A female patient, age 17, has white patches in her mouth, which are diagnosed as oral frictional hyperkeratosis. The patient is treated with a flavored oral rinse in the form of an emulsion containing 0.2% by weight of cyclosporin A in a castor oil water-containing carrier. This treatment is repeated three times daily for a week. After this period of treatment, and the removal of the frictional irritant which caused the condition, the white patches are resolved.

EXAMPLE 8

A female patient, age 70, presents with oral manifestations of an autoimmune blistering disease. Specifically, the patient is diagnosed with painful oral lesions resulting from pemphigus vulgaris. A gel containing 0.2% by weight cyclosporin A in a conventional carrier is topically applied to the lesions three times daily for two weeks. In addition, the patient undergoes oral hygiene therapy. After the two weeks, the patient reports that the pain from the lesions is reduced and the lesions are reduced in size.

EXAMPLE 9

A female patient, age 45, presents with bilateral striations on the buccal mucosa, tongue and gingivae which are diagnosed as oral lichen planus. The patient is treated with a flavored oral rinse in the form of an emulsion containing 0.2% by weight of cyclosporin A in a castor oil/water-containing carrier. After such treatment, the patient reports reduced pain and the striations are resolved.

EXAMPLE 10

A female patient, age 13, is diagnosed with aphthous ulcers in the oral cavity. The patient is treated with a flavored oral rinse in the form of an emulsion containing 0.2% by weight of cyclosporin A in a castor oil/water-containing carrier. After such treatment, the aphthous ulcers are resolved.

EXAMPLE 11

A male patient, age 52, presents with a number of abnormal lesions emanating from the nasal mucosa (nasal polyps). A composition containing 0.2% by weight of cyclosporin A and a conventional carrier, in the form of a nasal spray, is topically applied to the lesions three times a day for two weeks. After such treatment, the patient reports that the lesions have apparently been reduced in size because they cause less interference with air intake through the nose.

EXAMPLE 12

A male patient, age 35, is diagnosed with sinusitis. A composition containing 0.2% by weight of cyclosporin A and a conventional carrier, in the form of a nasal spray, is topically applied to the affected sinuses three times a day for two weeks. After such treatment, the patient reports that at least one symptom of the sinusitis is reduced.

EXAMPLE 13

A female patient, age 50, is diagnosed with an inflamed iris or iritis. A composition in the form of an emulsion containing 0.1% by weight of cyclosporin A in a castor oil/water-containing carrier is applied to the affected eye of the patient twice daily for two weeks. After such treatment, the iritis is resolved.

EXAMPLE 14

A male patient, age 45, is diagnosed with a carcinoid lung tumor. A suitable composition containing 0.3% cyclosporin A is injected into the affected area. Such injection is repeated twice over a two week period. Such treatment reduces the pain caused by the tumor. Surgery is employed to excise the tumor.

EXAMPLE 15

A male patient, age 35, is diagnosed with laryngitis. A composition containing 0.1% by weight of cyclosporin A in the form of a lozenge, is given to the patient three times daily for 1 week. Such treatment relieves the throat irritation caused by the laryngitis.

EXAMPLE 16

A male patient, age 65, is diagnosed with atrophic gastritis. The patient is treated by swallowing 10 ml of a flavored composition containing 0.3% by weight of cyclosporin A in an aqueous carrier. This treatment is repeated three times daily for two months. In addition, during this period, the patient takes an effective amount of an antimicrobial medication to resolve the helicobacter plylori infection, if any, that may be present. After this period of treatment, the patient reports a substantial reduction in at least one symptom of the atrophic gastritis.

While this invention has been described with respect to various specific examples and embodiments, it is to be understood that the invention is not limited thereto and that it can be variously practiced within the scope of the following claims.

What is claimed is:

1. A method of treating inflammatory bowel disease in a human or animal, the method comprising:

topically administering to a human or animal having inflammatory bowel disease a therapeutically effective amount of a cyclosporin A component selected from the group consisting of cyclosporin A, salts thereof and mixtures thereof, in a rectal suppository, thereby treating the inflammatory bowel disease.

2. The method of claim 1 wherein the administering step comprises topically administering the cyclosporin A component at or near a tissue area of the human or animal affected by the inflammatory bowel disease.

3. The method of claim 1 wherein the inflammatory bowel disease is ulcerative colitis.

4. The method of claim 1 wherein the cyclosporin A component is cyclosporin A.

5. The method of claim 1 wherein the treating comprises reducing the severity of at least one symptom of the inflammatory bowel disease.

6. The method of claim 1 wherein the cyclosporin A component is present in the rectal suppository in an amount of at least about 0.03% by weight.

7. The method of claim 1 wherein the cyclosporin A component is present in the rectal suppository in an amount in a range of about 0.1% to about 15% by weight.

8. A method of treating ulcerative colitis in a human or animal, the method comprising:

topically administering to a human or animal having ulcerative colitis a therapeutically effective amount of a cyclosporin A component selected from the group consisting of cyclosporin A, salts thereof and mixtures thereof, in a rectal suppository, thereby treating the ulcerative colitis.

9. The method of claim 8 wherein the administering step comprises topically administering the cyclosporin A component at or near a tissue area of the human or animal affected by the ulcerative colitis.

10. The method of claim 8 wherein the cyclosporin A component is cyclosporin A.

11. The method of claim 8 wherein the treating comprises reducing the severity of at least one symptom of the ulcerative colitis.

12. The method of claim 8 wherein the cyclosporin A component is present in the rectal suppository in an amount of at least about 0.03% by weight.

13. The method of claim 8 wherein the cyclosporin A component is present in the rectal suppository in an amount in a range of about 0.1% to about 15% by weight.

* * * * *